(12) United States Patent
Meisberger et al.

(10) Patent No.: US 9,364,654 B2
(45) Date of Patent: Jun. 14, 2016

(54) DEVICE FOR OPENING A LINE

(75) Inventors: Artur Meisberger, St. Wendel (DE);
Lars Michel, Rosbach v.d. Höhe (DE)

(73) Assignee: Fresenius Kabi Deutschland GmbH,
Bad Homburg (DE)

( * ) Notice: Subject to any disclaimer, the term of this patent is extended or adjusted under 35 U.S.C. 154(b) by 1148 days.

(21) Appl. No.: 13/123,271

(22) PCT Filed: Oct. 7, 2009

(86) PCT No.: PCT/EP2009/007203
§ 371 (c)(1),
(2), (4) Date: Apr. 8, 2011

(87) PCT Pub. No.: WO2010/040521
PCT Pub. Date: Apr. 15, 2010

(65) Prior Publication Data
US 2011/0198350 A1    Aug. 18, 2011

(30) Foreign Application Priority Data

Oct. 10, 2008  (DE) .................. 10 2008 051 163

(51) Int. Cl.
*F16K 7/02*       (2006.01)
*A61M 39/28*     (2006.01)
*A61M 1/02*      (2006.01)
*A61M 5/168*     (2006.01)

(52) U.S. Cl.
CPC ............. *A61M 39/283* (2013.01); *A61M 39/28* (2013.01); *A61M 1/0209* (2013.01); *A61M 5/16813* (2013.01); *F16K 7/02* (2013.01)

(58) Field of Classification Search
CPC . A61M 39/283; A61M 39/28; A61M 1/0209; A61M 5/16813; F16K 7/02; F16K 7/04; F16K 7/06; F16K 7/066
USPC ................. 251/253, 7, 8, 263, 4; 604/34, 250; 220/233; 137/554
See application file for complete search history.

(56) References Cited

U.S. PATENT DOCUMENTS

| 3,117,615 | A |   | 1/1964 | Graven |
| 3,266,287 | A |   | 8/1966 | Gill |
| 4,354,984 | A | * | 10/1982 | Richardson et al. ............ 261/66 |
| 4,496,133 | A | * | 1/1985 | Sule ................................. 251/7 |
| 4,596,374 | A | * | 6/1986 | Thompson et al. .............. 251/7 |
| 4,993,456 | A | * | 2/1991 | Sule ............................. 137/595 |

(Continued)

FOREIGN PATENT DOCUMENTS

DE    102005019855    11/2006
EP         0106182    4/1984
(Continued)

*Primary Examiner* — John K Fristoe, Jr.
*Assistant Examiner* — Andrew J Rost
(74) *Attorney, Agent, or Firm* — Occhiuti & Rohlicek LLP (57) ABSTRACT

The present application relates to a device for opening a line, particularly the line of a blood tube or blood bag system, wherein the line has a sealing element that blocks the line passage, wherein the device comprises at least one opening unit that is configured such that the same exerts a force acting upon the line from the exterior, whereby the sealing element is pressed together and the line is opened. The opening unit is contoured such that the line can be inserted into the opening unit only such that the force acting upon the line is exerted exclusively, or at least also in the region, in which the locking element is located.

24 Claims, 9 Drawing Sheets

(56) References Cited

U.S. PATENT DOCUMENTS

| | | | |
|---|---|---|---|
| 5,065,609 A | 11/1991 | Dischler | |
| 5,188,629 A * | 2/1993 | Shimoda | A61M 39/221 604/403 |
| 6,766,824 B2 * | 7/2004 | Taylor | 137/522 |
| 7,121,521 B2 * | 10/2006 | Lipscomb et al. | 251/8 |
| 8,087,635 B2 * | 1/2012 | Li et al. | 251/7 |
| 2008/0135115 A1 * | 6/2008 | Johansson et al. | 137/595 |

FOREIGN PATENT DOCUMENTS

| | | |
|---|---|---|
| EP | 1294061 | 3/2003 |
| WO | 03/081719 | 10/2003 |
| WO | 2004/058046 | 12/2003 |

* cited by examiner

DEVICE FOR OPENING A LINE

CROSS-REFERENCE TO RELATED APPLICATIONS

This application is the National Stage of International Application No. PCT/EP2009/007203, filed on Oct. 7, 2009, which claims the priority of German Patent Application No. 10 2008 051 163.3, filed on Oct. 10, 2008. The contents of both applications are hereby incorporated by reference in their entirety.

The present invention relates to a device for opening a line, more particularly the line of a blood-tube or blood-bag system, wherein the line has a sealing element that blocks the line passage, wherein the device has at least one opening apparatus that is designed such that it applies a force that acts on the line from the outside, as a result of which the sealing element is compressed and the line is opened.

By way of example, such a device for opening a line has been disclosed in DE 10 2005 019 855 A1. The opening apparatus disclosed therein consists of two jaws that are brought together in an automated fashion or by hand. In doing so, the line section located between the jaws is compressed and the sealing element is deformed plastically, and so a free flow-cross-section is created in the line and also remains free after the action of the opening apparatus.

The clinic staff and staff in blood banks often have to process relatively large numbers of blood-bag sets in order to separate blood into its constituents in a separator and store said constituents in separate containers. This is connected with relatively high demands on the staff because the continual opening of conventional sterile seals in particular requires considerable effort and can, in the long run, lead to pain amongst members of staff. Moreover, the staff are often under significant time pressure, and so the individual method steps have to be carried out over time periods of a few seconds.

Finally, there is the risk of operating errors and of the sterile seals inadvertently not, or only partly, being opened or having sharp edges in places. Particularly in the case of the presence of sharp edges in places, there is the risk of the blood constituents becoming damaged as a result of hemolysis.

It is therefore necessary to simplify and accelerate the method steps, and at the same time meet high safety and quality standards. This particularly holds true for the opening of sterile seals as have been disclosed in DE 10 2005 019 855 A1.

It is important that the opening apparatus for opening the sealing element operates in the shortest time possible and with the highest possible accuracy. In the process, fast and simple operation should be ensured, particularly in the case where the device is designed as a manually actuated device, such that high levels of acceptance are gained amongst users.

WO 2004/058046 A2 has disclosed a blood-processing instrument with an apparatus for opening sterile seals in blood tubes. This opening apparatus can be moved in the axial direction and, additionally, can be rotated. It serves for opening a sterile seal with a breaking cone. As explained above, such sterile seals are disadvantageous in that sharp edges and fragments of the sterile seal can be created in certain circumstances, and these can result in damage to the blood constituents. A further disadvantage of the arrangement described in WO 2004/058046 A2 consists of the fact that the described mechanism is comparatively complex because a continuous to-and-fro motion of the actuator has to be brought about. This is additionally also connected to a certain expenditure of time.

EP 1 294 061 B1 has disclosed a battery-operated pressing instrument for manual operation that works on hydraulic principles and has a comparatively complex design. Such constructions are comparatively difficult to use and cannot be used quickly, as is required for opening sterile seals in blood-bag or blood-tube systems quickly and with high precision.

Analogous remarks hold true for the electro-hydraulic handheld tool disclosed in WO 03/084719 A2, which serves for pressing tubular objects and cable lugs. The disclosed construction is comparatively complex and heavy, and therefore unsuitable for opening sterile seals.

Finally, EP 0 106 182 B1 has disclosed a tool for pressing sleeves, cable lugs or the like. This tool also operates on a hydraulic basis. It is unsuitable as a handheld tool for opening sterile seals.

The object of the present invention is to develop a device of the type mentioned at the outset such that it enables quick opening of sterile seals, as known from DE 10 2005 019 855 A1, and has a high accuracy.

This object is achieved by embodiments described herein.

Accordingly, provision is made for the opening apparatus to be contoured such that the line can only be introduced into the opening apparatus such that the force acting on the line is applied only in the region where the sealing element is located, or that said force is at least also applied therein. The line or the line section with the sealing element can thus only be introduced into the opening apparatus such that the force of pressure applied on the line from the outside acts at a pre-defined position and the line is thereby opened. Hence there is an operational connection within the meaning of a lock-and-key principle between the opening apparatus and the line section in question and this prevents a line section without the sealing element from inadvertently being introduced into the opening apparatus. This can reliably prevent the case where, although the opening apparatus is actuated, it does not lead to an opening of the line.

Hence, the correct introduction of the line section or line into the opening apparatus is supported by the aforementioned lock-and-key principle. In a preferred embodiment of the invention, provision is moreover made for means that prevent an only partial introduction of the line. Hence, the user of the device can be supported to the extent that actuation of the opening apparatus is prevented if the line has only been partly introduced into the opening apparatus. By way of example, these means can comprise a spring mechanism that is embodied such that the line is either pressed out of the opening apparatus or pressed into the correct position in the opening apparatus. Hence, this spring mechanism either presses incorrectly placed lines or line sections out of the opening apparatus or the receptacle thereof, or presses them into the correct position in which it is possible to open the sealing element.

The present invention moreover relates to a device for opening a line, more particularly the line of a blood-tube or blood-bag system, wherein the line has a sealing element that blocks the line passage, wherein the device has at least one opening apparatus that is designed such that it applies a force that acts on the line from the outside, as a result of which the sealing element is compressed and the line is opened. This device is characterized in that the device or opening apparatus has a processor unit that is designed such that, at certain times, it indicates or initiates the actuation of the opening apparatus to be undertaken and/or it only initiates this if the line is in the correct position thereof in the opening apparatus and/or it monitors the opening procedure of the sealing element.

Hence, it is for example feasible for the opening apparatus only to be activated if this is specified by the processor unit.

This may become necessary at a certain time within the process (e.g. the cell separation or any other type of blood treatment). If this is the case, the processor unit transmits a signal to the opening apparatus, as a result of which the opening apparatus is actuated and the sealing element is compressed, which results in the desired opening of the line.

Alternatively, or in addition thereto, provision can be made for the processor unit to be designed such that it only initiates the opening of the sealing element by the application of force if the line is in the correct position thereof in the opening apparatus. If this is not the case, provision can be made for the processor unit to prevent an actuation of the opening apparatus.

Alternatively, or in addition thereto, provision can be made for the processor unit to be designed such that it monitors the opening procedure of the sealing element. By way of example, this can be brought about by means of force-measuring elements, torque monitoring or measuring the motor current in a drive unit that actuates the opening apparatus. In the case of a missing line or line section, or if it has been introduced incorrectly or has not been opened flawlessly, provision can be made for the processor unit to interrupt the process and/or influence it in an otherwise expedient manner, for example by alerts or by generating an alarm signal.

Provision can be made for the opening apparatus to be designed such that in the case of a fault, if the line was placed incorrectly and the opening procedure was nevertheless initiated, the sealing element is not damaged to the extent where the sterility of the products is at risk. Thus, the opening procedure can for example be aborted in time and/or the sealing element may only be deformed so slightly that the line remains sealed and hence the sterility of the blood products remains ensured.

In a further embodiment of the invention, provision is made for the device or the opening apparatus to have at least one sensor that is designed such that it registers the presence of the line in the opening apparatus and/or the position thereof in the opening apparatus and/or at least one parameter characteristic for the opening procedure of the sealing element. As explained previously, this at least one characteristic parameter can be the force, the torque or the motor current or the like, which occur when the sealing element is opened.

In a preferred embodiment of the invention, provision is made for the sensor to be connected to the processor unit, wherein the processor unit is designed such that it only initiates the actuation of the opening apparatus when the line is in the correct position in the opening apparatus, said position being registered by the sensor.

Provision can furthermore be made for the sensor of the opening apparatus to be connected to the processor unit and for the processor unit to be designed such that it interrupts the opening procedure of the sealing element and/or emits an alert, which the user of the device can identify, if the opening procedure deviates from an intended progression. By way of example, this can be the case if the opening procedure was initiated without the line being placed correctly into the opening apparatus.

The present invention can be embodied in the form of a handheld tool, that is to say in the form of a handheld apparatus. This handheld apparatus is preferably used in methods in which there is at least some manual handling of blood-bag systems for cell separation or for any other blood treatment. However, the invention is not restricted to these but rather also comprises e.g. blood-treatment machines that are formed by the device according to the invention or that have the device according to the invention as a constituent part. In the case of these blood-processing machines, provision can be made for using predominately automated processes for cell separation or any other blood treatment. Provision is preferably made for the sealing element to be likewise opened in an automated fashion or to be initiated at a certain time within the process.

If the tool is a handheld apparatus, provision can be made for a wired or wireless connection to provide a communication link between the handheld apparatus and the processor unit of the device. By way of example, this communication link serves for displaying information on the handheld instrument, such as a user guide that shows the user which sealing element has to be opened at what time by means of the handheld apparatus. In this case, the handheld tool can be operated particularly easily and quickly because the user is advised, for example on a display or acoustically or in any other way, that the sealing element has to be opened or which sealing element has to be opened.

By way of example, the aforementioned processor unit can be arranged in a blood-processing machine and the sensor or sensors can be arranged in the handheld apparatus.

However, as explained above, the invention is not restricted to handheld apparatuses but likewise comprises the case where the at least one opening apparatus is a component of a larger unit, more particularly a blood-processing machine.

In addition to the aforementioned features, the device can also have the feature that the introduction of the line section into the opening apparatus operates according to the lock-and-key principle, as a result of which the introduction of line sections without a sealing element can be prevented.

The invention furthermore relates to a device for opening a line, more particularly the line of a blood-tube or blood-bag system, wherein the line has a sealing element that blocks the line passage, wherein the device has at least one opening apparatus that is designed such that it applies a force that acts on the line from the outside, as a result of which the sealing element is compressed and the line is opened. The device is characterized in that the opening apparatus has an opening element and a drive unit, wherein the opening element or the drive unit is connected to a guide and the drive unit or the opening element is connected to a rotational or sliding body, the latter running along the guide and being put into a rotational motion relative to the guide when the drive unit is operated, wherein the guide is designed such that the relative motion between the rotational or sliding body and guide results in an extension or retraction movement of the opening element.

Hence, it is feasible, for example, for the drive unit to be connected to a rotational or sliding body, which is put into a rotational motion when the drive unit is operated. This rotational or sliding body runs in or on a guide, which is designed such that the aforementioned rotational motion of the rotational or sliding body leads to an extension movement of the opening element. In doing so, provision can be made for the guide to be fixedly connected to the opening element and the rotational or sliding body to be fixedly connected to the drive unit. In principle, it is likewise feasible for the guide to be arranged on the drive unit and the rotational or sliding body to be arranged on the opening element. What is essential is that the relative motion between rotational and sliding body and the guide leads to an extension movement or to a retraction movement of the opening element.

The opening element can be spring-loaded, wherein the spring is arranged such that it applies a force onto the opening element or a component connected thereto, which force is directed counter to the extension movement. Hence the spring element ensures that the opening element is once again retracted once the latter is no longer required for opening the line.

The guide can be designed such that there is a constant or substantially constant torque of the drive unit during the extension movement of the opening element. Provision is preferably made for a largely constant torque to be required for providing the force, which increases continuously to a maximum value, and the opening of the sealing element. As a result, use can be made of a comparatively small, light and inexpensive drive.

This embodiment is particularly advantageous if the device is used as a handheld device. By way of example, it is feasible that only one or optionally also a plurality of such handheld instruments are required for a blood-processing machine. The user then only needs to open the sealing element, or successively open the various sealing elements, as per the user guide. Here, the communication with the processor unit can, as explained above, be brought about over wires or radio communication.

However, the invention is not restricted to this, but likewise comprises opening apparatuses that bring about the opening of the sealing elements according to a simple pliers principle with a flat or angled drive.

As explained above, the device can be a blood-treatment instrument, more particularly an instrument for cell separation. However, the invention is not restricted to this.

The term "line" should be understood broadly and comprises any region through which a fluid can flow, such as line sections, tubes and connector regions e.g. of blood-bag systems.

Further details and advantages of the invention are explained in more detail on the basis of an exemplary embodiment illustrated in the drawing, in which:

FIGS. 1, 2, FIGS. 7-12: show detailed illustrations of the rotational body and the guide with opening element.

Figure 1:
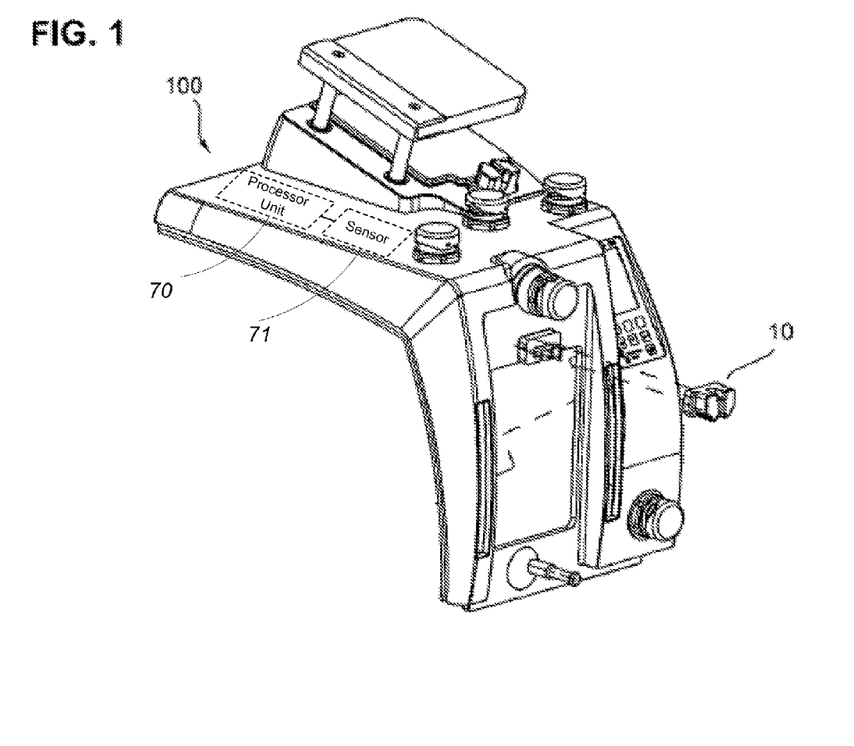
FIG. 1: shows a perspective illustration of part of a blood-treatment apparatus with opening apparatus.

FIG. 1 illustrates a perspective illustration of a part 100 of a blood-treatment instrument for cell separation. On its front side, this instrument has an opening apparatus 10 that serves for opening a sealing element as described in detail in DE 10 2005 019 855 A1. In this respect, reference is made to said document.

The opening apparatus 10 is activated at certain times by a processor unit (illustrated schematically) of the instrument to bring about the compression of the sealing element and hence the 30 opening of the line.

Figure 2A:
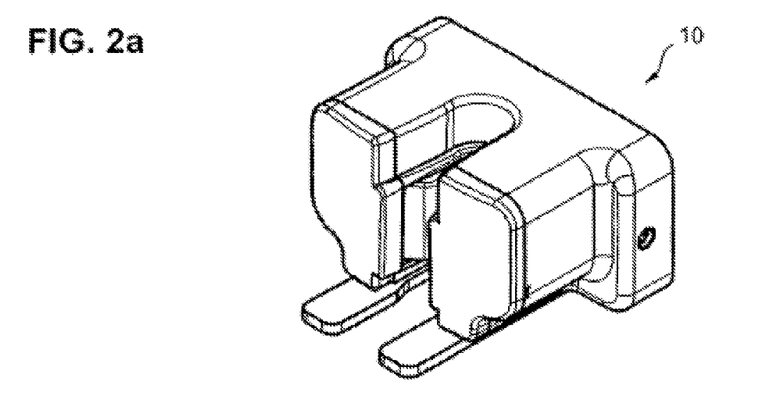
FIGS. 2a and 2b: show a perspective illustration of an opening apparatus in both an assembled state and an exploded view.
Figure 2B:
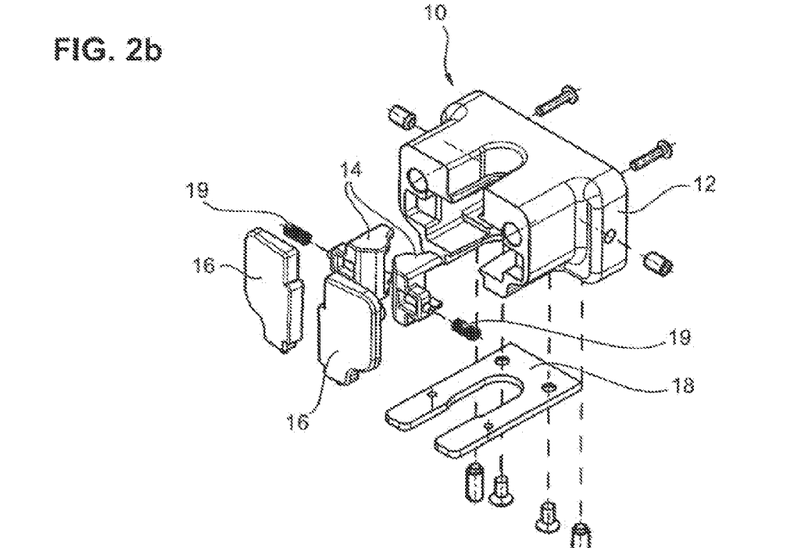

FIG. 2a shows the opening apparatus 10 in an enlarged perspective illustration; FIG. 2b shows the arrangement in an exploded illustration. The reference sign 12 denotes the housing of the arrangement. The reference sign 14 denotes the two elements, which interact like pliers, of a mechanism that prevents the tube section from only partly being introduced into the illustrated opening apparatus 10. It emerges from FIG. 2b that these two jaws 14 are loaded by springs 19. The effect of these spring-loaded jaws 14 is that a tube, provided that it was only partly introduced, either is completely pressed into the opening apparatus or is pressed out again. The actual jaws, which preferably interact like pliers, or pliers for opening the sealing element are, from the point of view of the observer, behind the region delimited by the jaws 14 and are not illustrated in the figures.

Hence, the correct introduction of the line section into the opening apparatus 10 for opening the sealing element can be supported by a mechanism like the one shown in FIG. 2b in the form of the spring-loaded jaws 14.

The reference sign 16 denotes the front-side cover and the reference sign 18 denotes the base-side cover, which additionally serves as a breaking apparatus for standard connections.

The opening apparatus 10 as per FIGS. 1, 2 operates according to the pliers-principle. It can have a flat or an angled drive. The contour of the opening apparatus 10 is formed such that the sealing elements, or the line sections containing these, can only be introduced such that they are pressed at the predetermined location and hence the lines are opened. This lock-and-key principle prevents the inadvertent introduction of line sections in which no such sealing element is arranged. The result of this would be that although the opening apparatus is actuated, this would not result in an opening of the line.

Figure 2C:
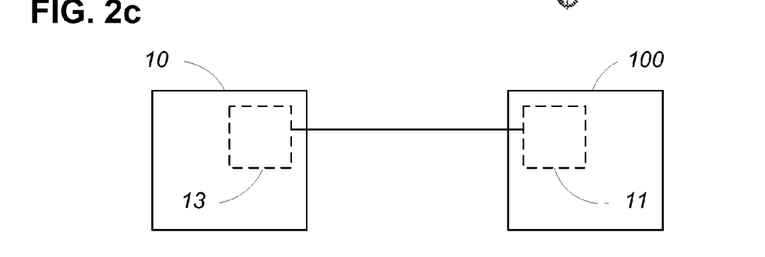
FIG. 2c: shows a block diagram of the opening apparatus and a part of a blood treatment instrument.

The opening apparatuses 10 are furthermore connected to a processor unit 11, FIG. 2c, that obtains information from a sensor 13 of the opening apparatus 10 that a line section with a sealing element has been introduced and is in the correct position. During the opening procedure, this processor unit 11 monitors the flawless progression of said opening procedure, which monitoring can for example be brought about by means of a force-measuring element, torque monitoring or measuring the motor current. In the case of an incorrectly introduced or missing line section or sealing, or if the sealing element has not been opened flawlessly, the processor unit 11 can, for example, interrupt or abort the opening process or trigger an alert or alarm.

The opening apparatus according to the invention can be combined with an aid for opening standard seals (reference sign 18 in FIG. 2b), which are opened by bending. It can be designed such that the use of conventional blood-bag systems is not a hindrance, but is supported by the aforementioned breaking aid.

FIGS. 3 to 18 relates to a handheld apparatus 20 for opening sealing elements as have been disclosed in DE 10 2005 019 855 A1.

Figure 3:
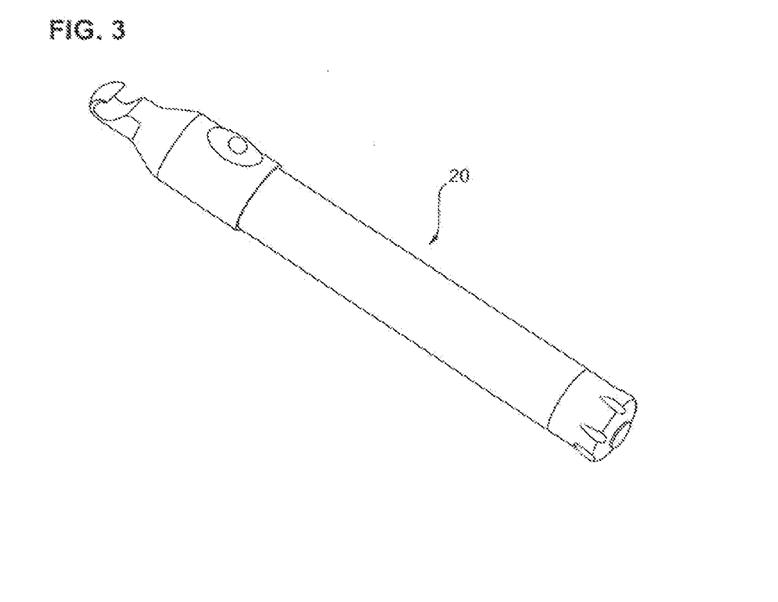
FIGS. 3, 4: show a handheld device for opening sterile seals in both a perspective view and a section.
Figures 4, 5:
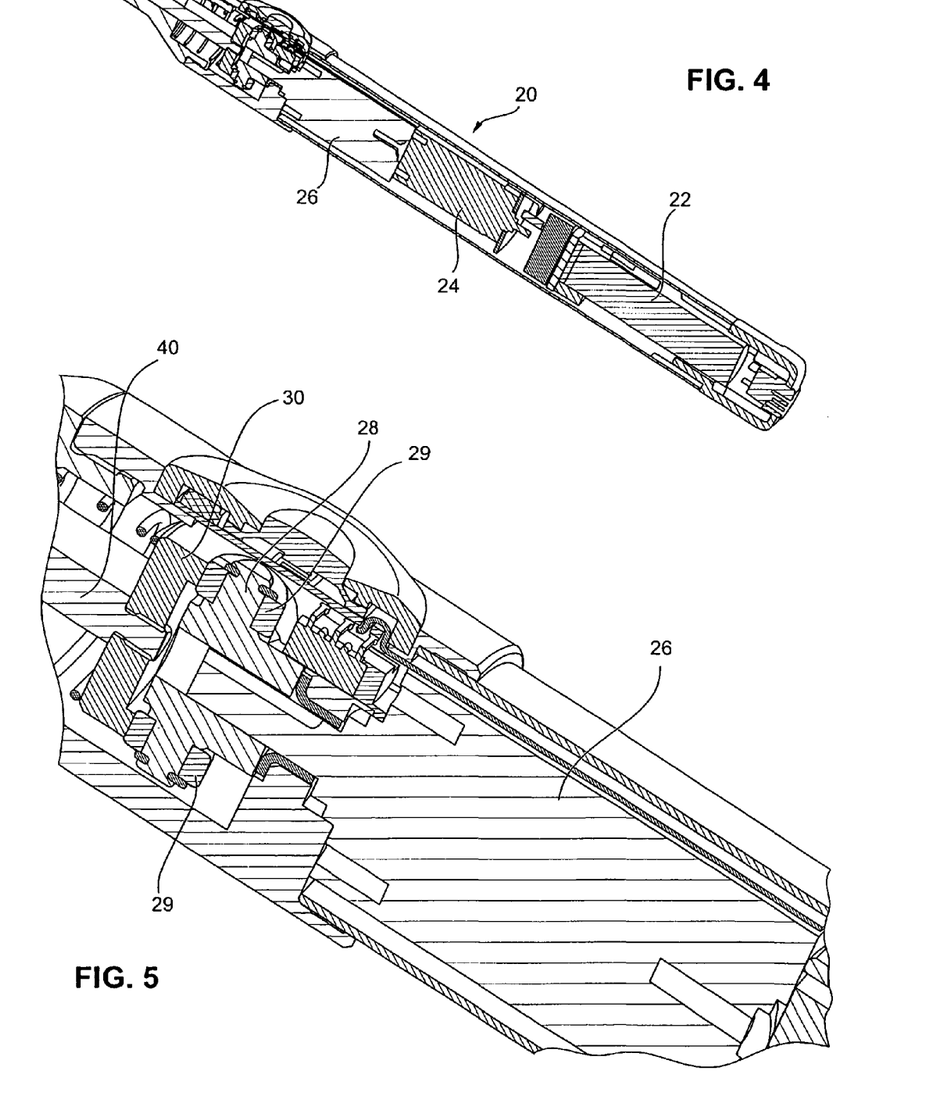
FIGS. 5, 6: show detailed illustrations of the guide and the rotational body of the apparatus as per
Figure 6:
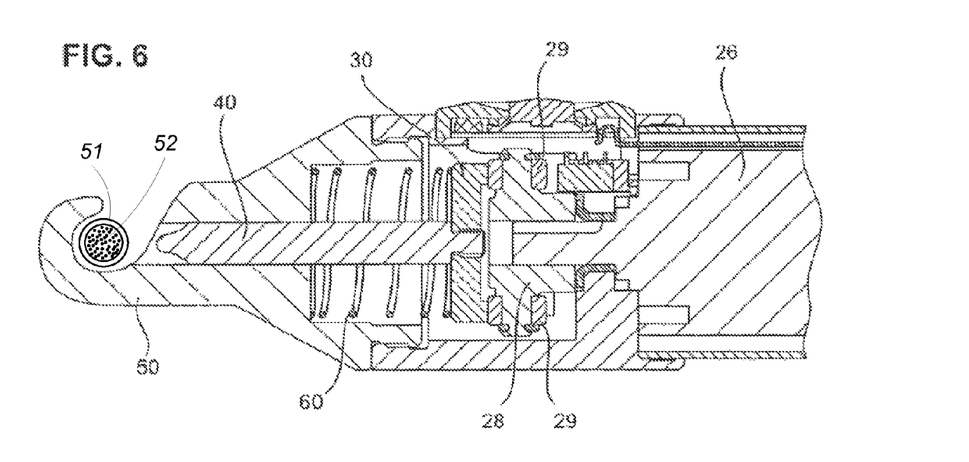
Figure 7:
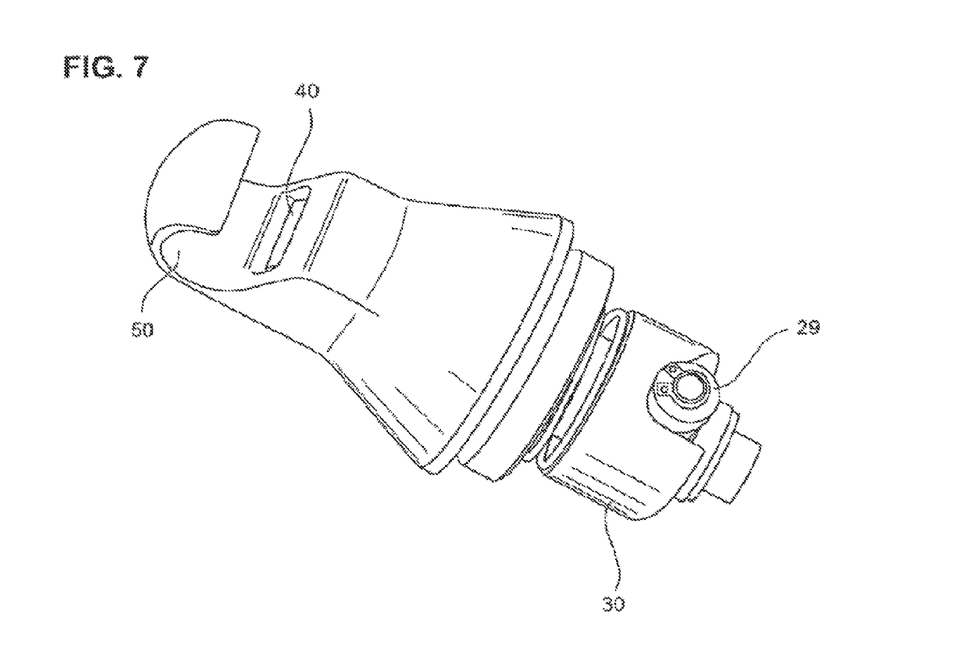
Figure 8:
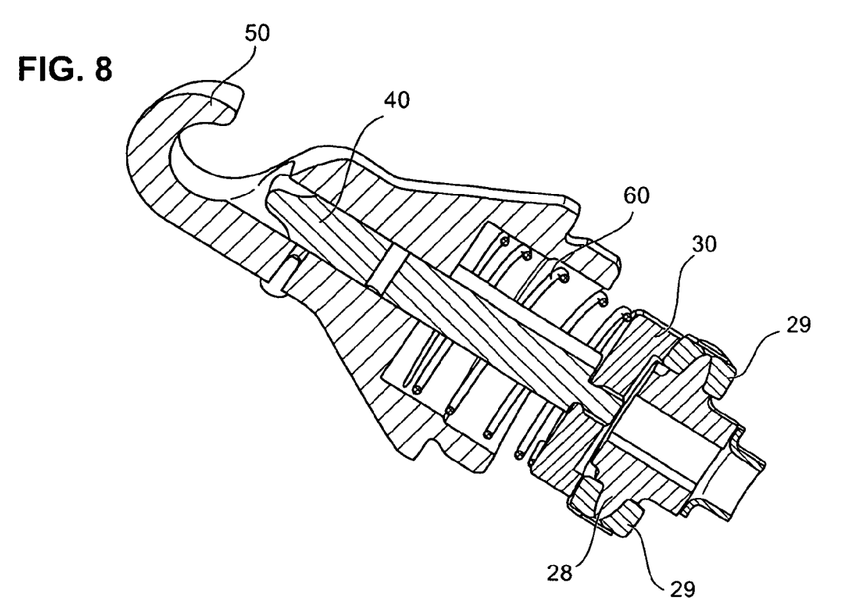
Figure 9:
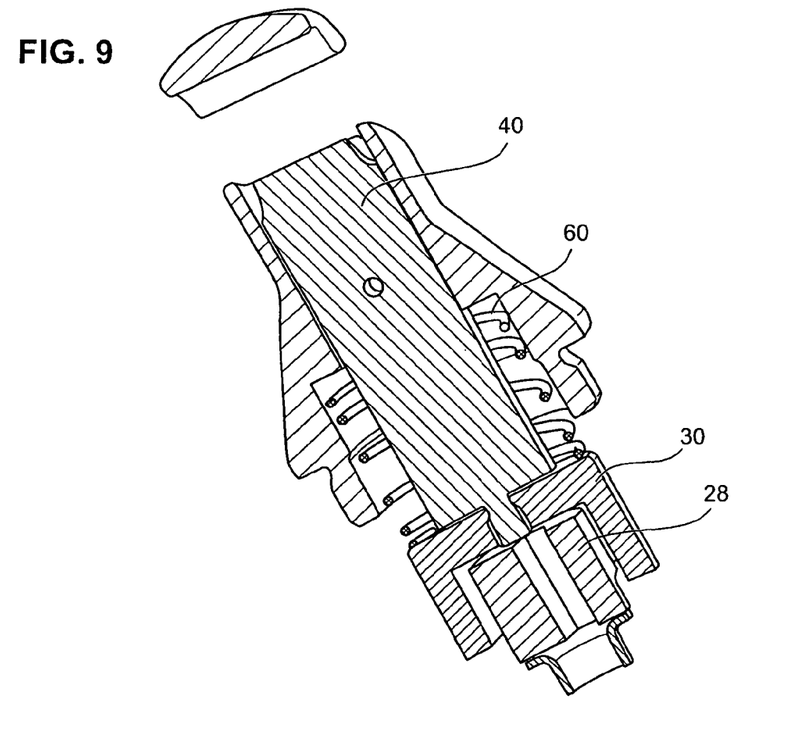
Figure 10:
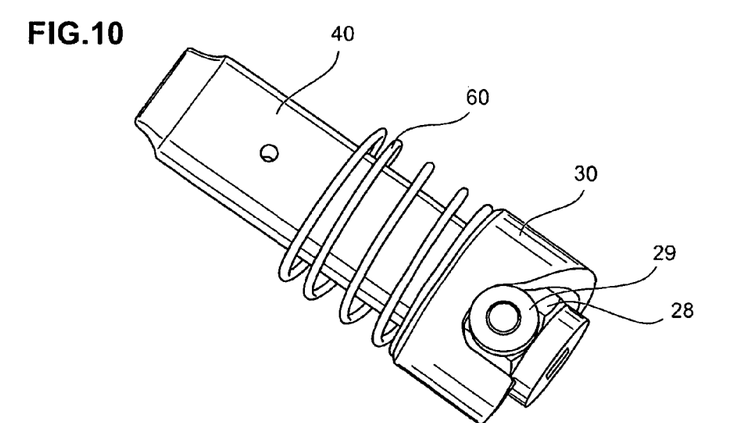
Figure 11:
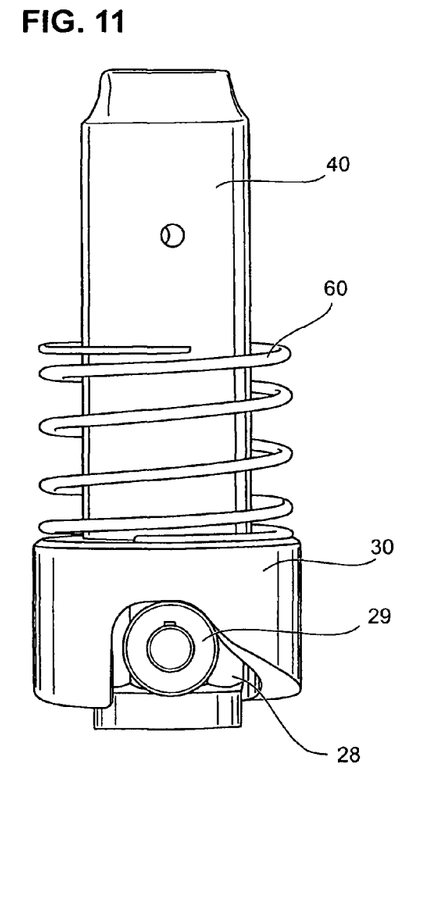
Figure 12:
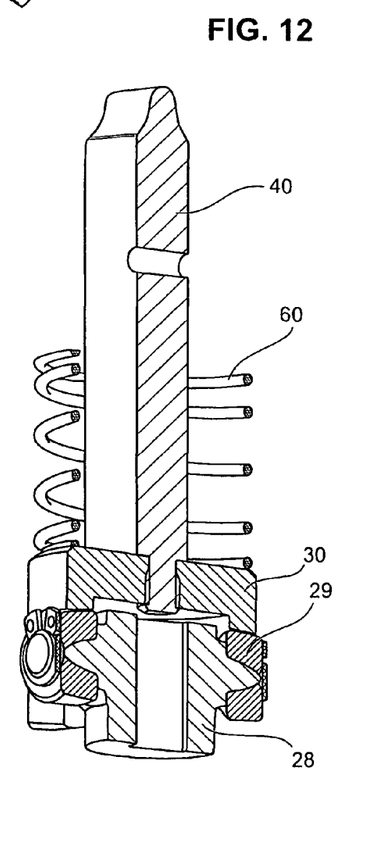
Figure 13:
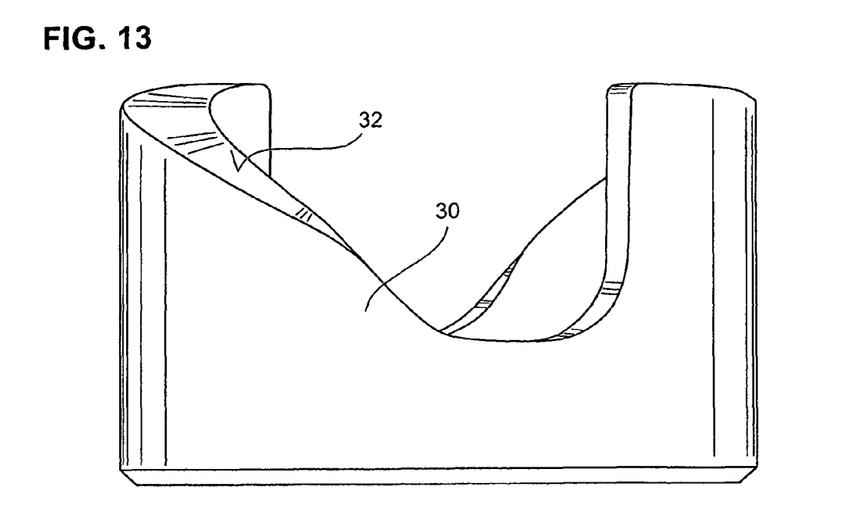
FIGS. 13-18: show different views and contour illustrations of the guide of the apparatus as per FIGS. 3, 4.
Figure 14:
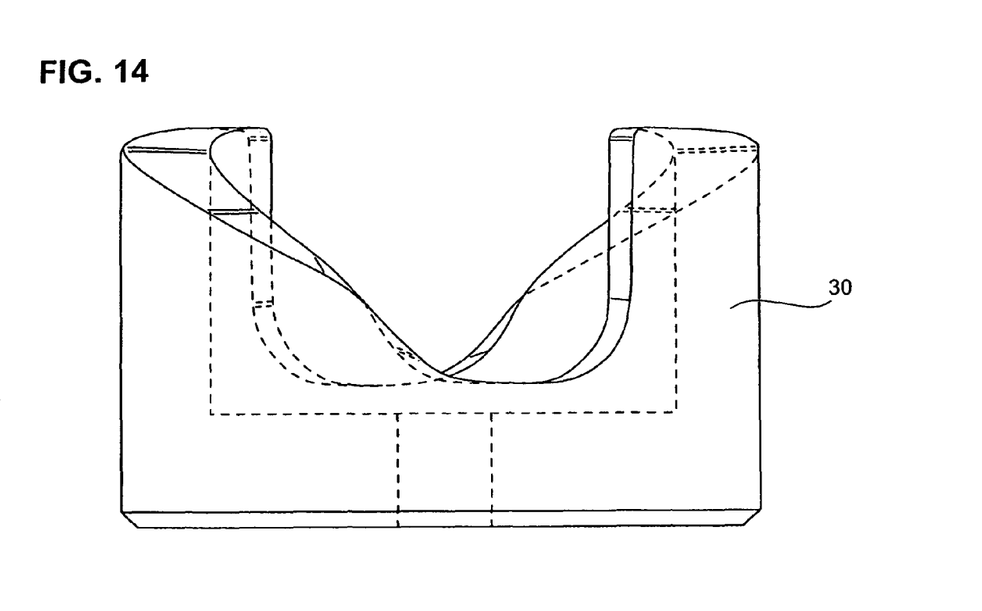
Figure 15:
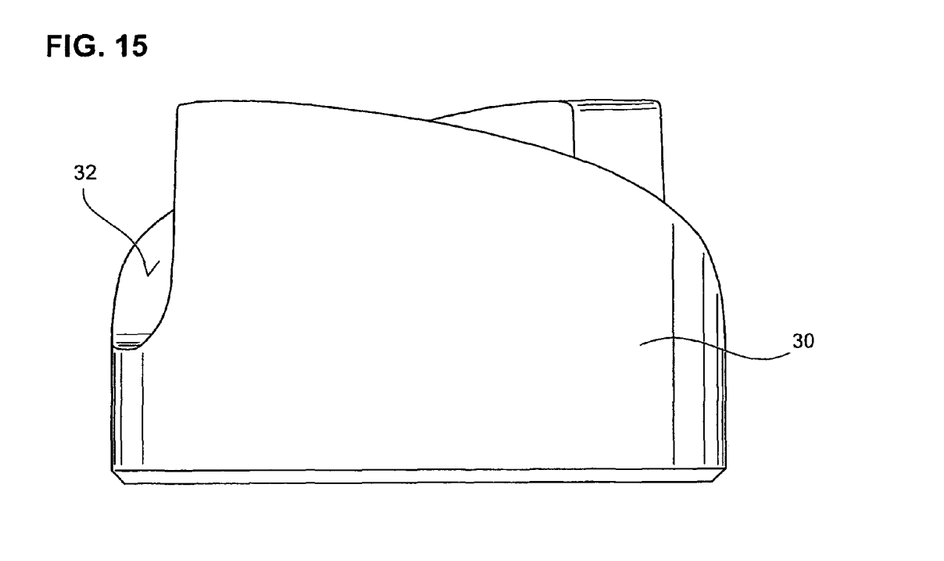
Figure 16:
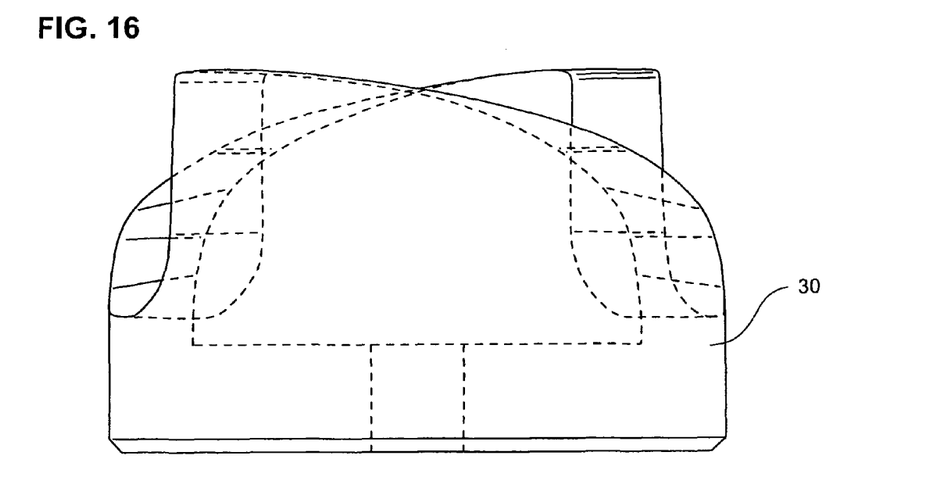
Figure 17:
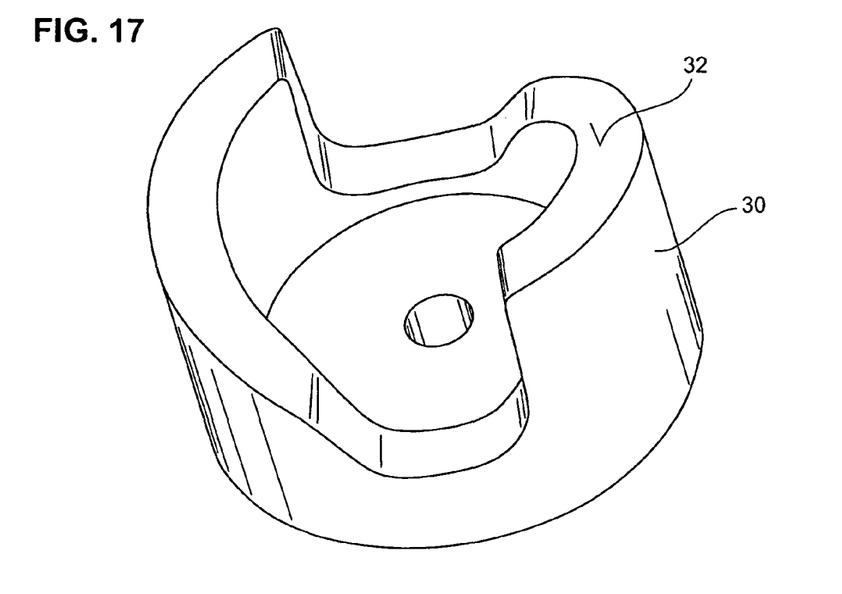
Figure 18:
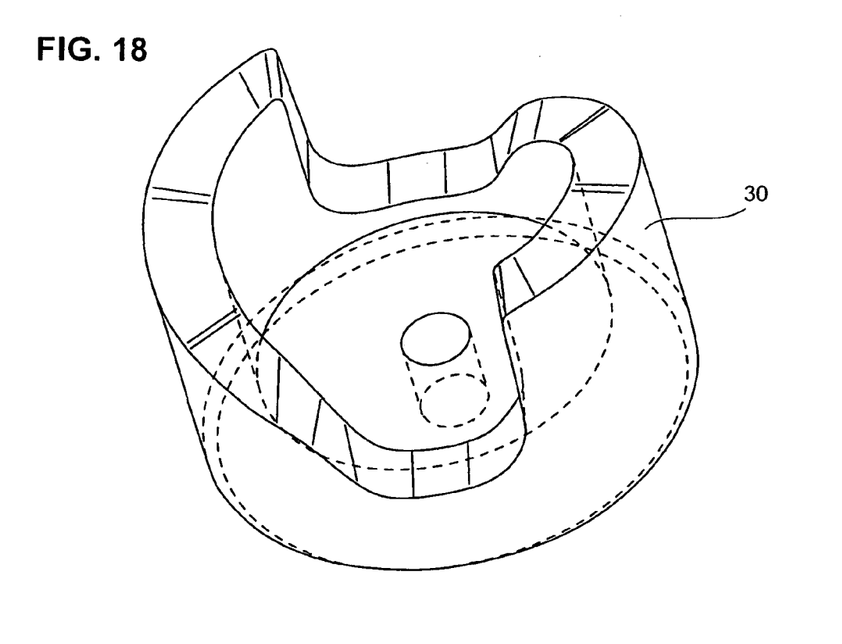

The handheld apparatus has a rod-shaped form; this is shown in FIGS. 3 and 4. It has a rechargeable battery or a battery 22, which drives a DC motor 24. When the motor 24 is actuated, the rotational body 28 is driven, i.e. put into a rotational motion, by the transmission 26 connected to the motor 24. The rotational body 28 has axes in its two diametrically opposed regions, on which rotatable wheels 29 are arranged. By way of example, this emerges from the detailed illustrations in FIGS. 5 and 6. These wheels 29 run in a guide 30, which in turn is connected in a non-rotatable fashion to an opening element 40, which emerges from FIG. 6 in particular. FIGS. 7 to 12 again show the arrangement of the guide and the wheels 29 driven by the rotational body 28 in various perspective and sectional views.

If the rotational body 28 is actuated by the motor 24 or via the transmission 26, the wheels 29 roll on the surface of the guide 30, which leads to an axial extension or retraction movement of the opening element 40. FIGS. 6-9 show the opening element in the refracted position. If a sterile seal should be opened, the corresponding line section 51 is introduced into the hook shaped end region 50 of apparatus 20 and thereupon the opening element 40 is extended as a result of the user actuating a push-button such that the sealing element 52 is compressed and hence the line 51 is opened. The return movement of the opening element is brought about by the spring 60, which emerges from FIGS. 7 to 12 in particular. When the opening element is actuated, it partly enters this hook-shaped end section or the clear space formed by the latter and thus compresses the line 51.

It is feasible for the apparatus as per FIGS. 3, 4 to have a sensor that automatically identifies that the line was introduced correctly and automatically initiates the opening procedure. It is likewise feasible for the user to be prompted by a user guide to bring about an extension movement of the opening element 40 by actuating a push-button or a switch.

By way of example, the apparatus as per FIGS. 3, 4 can be connected to the blood-treatment instrument over a wired connection, or else wirelessly, and can obtain the corresponding signals therefrom. The communication between these two units can also be bi-directional and for example comprise the transfer of data from which it emerges that the opening procedure has taken place.

FIGS. 13 to 18 show different perspective illustrations of the guide 30 and the contour lines thereof. The guide 30 is substantially designed as a hollow-cylinder section and has the guide surface 32 on the end side in an end region, with the wheels or sliding bodies or the like, which can be put into a rotational motion by the drive unit, running on said guide surface. Here, the contour of the surface 32 of the guide 30 is embodied such that it does not have a constant incline, but that an almost constant torque is required for applying the force for opening the sealing element, which force increases continuously to a maximum value. The advantage of such an embodiment is that the drive can have a comparatively small, light and inexpensive design.

The invention claimed is:

1. A device for opening a line that includes a tube in which a sealing element configured to block fluid flow within the line is disposed, the device comprising:
at least one opening apparatus that is operable to apply an external force on the line to compress the sealing element and open the line, the opening apparatus being contoured to receive the line such that the external force is applied substantially in a region of the line where the sealing element is located;
means for preventing a partial receipt of the line by the opening apparatus, the means including a spring mechanism that is operable to move the line from a partially received state out of the opening apparatus or to move the line from a partially received state into a correct position in the opening apparatus
wherein the spring mechanism includes a first inclined surface for moving the line from the partially received state out of the opening apparatus, and a second inclined surface for moving the line from the partially received state into the correct position in the opening apparatus; and wherein the first inclined surface and the second inclined surface intersect.

2. The device of claim 1, wherein the external force is applied only in the region of the line where the sealing element is located.

3. The device of claim 1, wherein the device is a blood-treatment instrument or a component of a blood treatment instrument.

4. The device of claim 1, wherein at least one of the device and the opening apparatus has at least one sensor that is configured to perform at least one of the following: register a presence of the line in the opening apparatus, register a position of the line relative to the opening apparatus, and register at least one parameter characteristic for a procedure for opening the sealing element.

5. The device of claim 1, wherein the opening apparatus is a component of a handheld apparatus.

6. The device of claim 1 wherein the first inclined surface faces away from the second inclined surface.

7. The device of claim 6 wherein the first inclined surface and the second inclined surface together have a substantially bell shaped profile.

8. A device for opening a line that includes a tube in which a sealing element configured to block fluid flow within the line is disposed, the device comprising:
at least one opening apparatus that is operable to apply an external force on the line to compress the sealing element and open the line,
means for preventing a partial receipt of the line by the opening apparatus, the means including a spring mechanism that is operable to move the line from a partially received state out of the opening apparatus or to move the line from a partially received state into a correct position in the opening apparatus; wherein the spring mechanism includes a first inclined surface for moving the line from the partially received state out of the opening apparatus, and a second inclined surface for moving the line from the partially received state into the correct position in the opening apparatus; and wherein the first inclined surface and the second inclined surface intersect; and
wherein at least one of the device and the opening apparatus has a processor unit that is operable to perform one or more of the following actions: indicate a need to actuate the opening apparatus, initiate an actuation of the opening apparatus, initiate an actuation of the opening apparatus only if the line is in a correct position relative to the opening apparatus, and monitor a procedure for the opening of the line.

9. The device of claim 8, wherein at least one of the device and the opening apparatus has at least one sensor that is configured to perform at least one of the following: register a presence of the line in the opening apparatus, register a position of the line relative to the opening apparatus, and register at least one parameter characteristic for a procedure for opening the sealing element.

10. The device of claim 8, wherein a sensor is connected to the processor unit, and the processor unit is operable to initiate the actuation of the opening apparatus when the line is in the correct position relative to the opening apparatus, said position being registered by the sensor.

11. The device of claim 10, wherein the sensor is connected to the processor unit, and the processor unit is operable to perform one or more of the following: interrupt the procedure for opening the sealing element, and emit an alert, which the user of the device can identify, if the procedure for opening the sealing element deviates from an intended progression.

12. The device of claim 8, wherein the opening apparatus is a component of a handheld apparatus.

13. The device of claim 12, wherein the handheld device comprises means for indicating to a user of the handheld devices that an opening procedure of a sealing element is to be undertaken.

14. The device of claim 8, wherein the opening element includes a spring that is arranged to apply a force onto the opening element or a component connected thereto, which force is directed counter to the extension movement.

15. The device of claim 8, wherein a guide is configured such that a constant or substantially constant torque of a drive unit is required for the extension movement of the opening element while the line is being compressed.

16. The device of claim 8, wherein the opening apparatus is contoured to receive the line such that the external force is applied substantially in a region of the line where the sealing element is located.

17. The device of claim 8, wherein the device is a blood-treatment instrument or a component of a blood treatment instrument.

18. A device for opening a line having a sealing element configured to block fluid flow within the line, the device comprising:
- at least one opening apparatus that is operable to apply an external force on the line to compress the sealing element and open the line, the opening apparatus having an opening element and a drive unit,
- means for preventing a partial receipt of the line by the opening apparatus, the means including a spring mechanism that is operable to move the line from a partially received state out of the opening apparatus or to move the line from a partially received state into a correct position in the opening apparatus, wherein the spring mechanism includes a first inclined surface for moving the line from the partially received state out of the opening apparatus, and a second inclined surface for moving the line from the partially received state into the correct position in the opening apparatus; and wherein the first inclined surface and the second inclined surface intersect; and
wherein:
- at least one of the opening element and the drive unit is connected to one or more of a guide, a rotational body, and a sliding body,
- the rotational body is put into a rotational motion relative to the guide when the drive unit is operated, and
- the guide is configured such that a motion of the rotational body or the sliding body relative to the guide results in an extension or retraction movement of the opening element.

19. The device of claim 18, wherein the opening element is contoured to receive the line such that the external force is applied substantially in a region of the line where the sealing element is located.

20. The device of claim 18, wherein at least one of the device and the opening element has a processor unit that is operable to perform one or more of the following actions: indicate a need to actuate the opening apparatus, initiate an actuation of the opening apparatus, initiate an actuation of the opening apparatus only if the line is in a correct position relative to the opening apparatus, and monitor a procedure for the opening of the line.

21. The device of claim 18, wherein at least one of the device and the opening apparatus has at least one sensor that is configured to perform at least one of the following: register a presence of the line in the opening apparatus, register a position of the line relative to the opening apparatus, and register at least one parameter characteristic for a procedure for opening the sealing element.

22. The device of claim 21, wherein the sensor is connected to the processor unit, and the processor unit is operable to initiate the actuation of the opening apparatus when the line is in the correct position relative to the opening apparatus, said position being registered by the sensor.

23. The device of claim 22, wherein the sensor is connected to the processor unit, and the processor unit is operable to perform one or more of the following: interrupt the procedure for opening the sealing element, and emit an alert, which the user of the device can identify, if the procedure for opening the sealing element deviates from an intended progression.

24. The device of claim 18, wherein the device is a blood-treatment instrument or a component of a blood treatment instrument.

* * * * *